United States Patent [19]
Chen et al.

[11] Patent Number: 5,824,837
[45] Date of Patent: Oct. 20, 1998

[54] EXPRESSION OF HUMAN INTERLEUKIN-1β IN A TRANSGENIC ANIMAL

[75] Inventors: Howard Y. Chen, Westfield, N.J.; Kathryn J. Hofmann, Collegeville, Pa.; Leonardus H. T. Van Der Ploeg, Scotch Plains, N.J.; Alan R. Shaw, Doylestown, Pa.; Myrna E. Trumbauer, Yardley, Pa.; Hui Zheng, Edison, N.J.

[73] Assignee: Merck & Co., Inc., Rahway, N.J.

[21] Appl. No.: 571,983

[22] PCT Filed: Jul. 19, 1994

[86] PCT No.: PCT/US94/08111

§ 371 Date: Apr. 22, 1996

§ 102(e) Date: Apr. 22, 1996

[87] PCT Pub. No.: WO95/03402

PCT Pub. Date: Feb. 2, 1995

Related U.S. Application Data

[63] Continuation-in-part of Ser. No. 96,943, Jul. 22, 1993, abandoned.

[51] Int. Cl.⁶ .............. A61K 49/00; C12N 5/18; C12N 15/09; C12N 15/16
[52] U.S. Cl. .............. 800/2; 424/9.1; 424/9.2; 435/172.3; 536/23.51; 536/24.1
[58] Field of Search .............. 800/2; 424/9.1, 424/9.2; 536/23.51, 24.1; 435/172.3

[56] References Cited

FOREIGN PATENT DOCUMENTS

| 0 169 672 | 6/1985 | European Pat. Off. . |
| 9113979 | 9/1991 | WIPO . |

OTHER PUBLICATIONS

Bradley, et al., "Modifying the Mouse: Design and Desire", Bio. Technology, vol. 10, pp. 534–539 (1992).

Capecchi, Altering the Genome by Homologous Recombination, Science, vol. 244, pp. 1288–1292 (1989).

Capecchi, et al., "The New Mouse Genetics: Altering the Genome by Gene Targeting", Trends in Genetics, vol. 5, pp. 70–76 (1989).

Frohman, et al., "Cut, Paste & Save: New Approaches to Altering Specific Genes in Mice", Cell, vol. 56, pp. 145–147 (1989).

Jaenisch, "Transgenic Animals", Science, vol. 240, pp. 1468–1474 (1988).

Wagner, "On Transferring Genes into Stem Cells and Mice", The EMBO Journal, vol. 9, pp. 3025–3032 (1990).

Velander, et al., "Production of Biologically Active Human Protein C in the Milk of Transgenic Mice", Animals of the NY Acad. of Sci., vol. 665, pp. 391–403 (1992).

Goldgaber, et al., "Interleukin 1 Regulates Synthesis of Amyloid B–Protein precursor mRNA in Human Endothelial Cells", Proc. Natl. Acad. Sci., vol. 86, pp. 7606–7610 (1989).

Vandenabeele, et al., "Is Amyloidogenesis During Alzheimer's Disease Due to an IL–1/IL–6–Mediated 'Acute Phase Response' in the Brain", vol. 12, pp. 217–219 (1991).

Tocci, et al., "Expression in *Escherichia Coli* of Fully Active Recombinant Human IL 1B: Comparison with Native Human IL 1B", J. Immunol. vol. 138, pp. 1109–1114 (1987).

Tocci et al J. Immunol 138 1109, 1987.

Vandenabeele 12 217, 1991.

*Primary Examiner*—Brian R. Stanton
*Attorney, Agent, or Firm*—Joseph A. Coppola; Jack L. Tribble

[57] ABSTRACT

A transgenic mouse has been prepared that expresses a human interluekin-1β transgene. Expression of the transgene is mediated by a mouse metallothionein promoter. As a result of the expression of this transgene, the mouse has inflammation of its kidney and liver. The claimed animals are useful as screening tools for agents that are potentially useful for treating inflammation.

3 Claims, No Drawings

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
TAATACGACT CACTATAGGG                                                        20
```

( 2 ) INFORMATION FOR SEQ ID NO:2:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
ACGTCGACTC TAGAAGATCT TCGACTCGAG ATCGATGGTA CCCGGGCAGG TTCAAGCTTC            60
TGGGATTGGG ATCTCAGTC                                                         79
```

( 2 ) INFORMATION FOR SEQ ID NO:3:

( i ) SEQUENCE CHARACTERISTICS:
        ( A ) LENGTH: 174 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
CGATGGAACC ATGGAAATCT GCAGGGGACC TTACAGTCAC CTAATCTCTC TCCTTCTTAC            60
CTTGGTACCT TTAGACGTCC CCTGGAATGT CAGTGGATTA GAGAGAGGAA GACATCCTTC           120
TGTTTCATTC AGAGGCAGCC TGCGTAGGAA GACAAAGTAA GTCTCCGTCG GACG                 174
```

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
GCACCTGTAC GATCACTGAA CTGC                                                   24
```

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single ( D ) TOPOLOGY: linear ( i i ) MOLECULE TYPE: cDNA ( x i ) SEQUENCE DESCRIPTION: SEQ ID NO:5:

GAAGATCTAG GAAGACACAA ATTGCATGGT GAAG 34

( 2 ) INFORMATION FOR SEQ ID NO:6:

( i ) SEQUENCE CHARACTERISTICS:
         ( A ) LENGTH: 23 base pairs
         ( B ) TYPE: nucleic acid
         ( C ) STRANDEDNESS: single
         ( D ) TOPOLOGY: linear ( i i ) MOLECULE TYPE: cDNA ( x i ) SEQUENCE DESCRIPTION: SEQ ID NO:6:

GGCATTCCAC CACTGCTCCC ATT 23

( 2 ) INFORMATION FOR SEQ ID NO:7:

( i ) SEQUENCE CHARACTERISTICS:
         ( A ) LENGTH: 24 base pairs
         ( B ) TYPE: nucleic acid
         ( C ) STRANDEDNESS: single
         ( D ) TOPOLOGY: linear ( i i ) MOLECULE TYPE: cDNA ( x i ) SEQUENCE DESCRIPTION: SEQ ID NO:7:

GCACCTGTAC GATCACTGAA CTGC 24

( 2 ) INFORMATION FOR SEQ ID NO:8:

( i ) SEQUENCE CHARACTERISTICS:
         ( A ) LENGTH: 22 base pairs
         ( B ) TYPE: nucleic acid
         ( C ) STRANDEDNESS: single
         ( D ) TOPOLOGY: linear ( i i ) MOLECULE TYPE: cDNA ( x i ) SEQUENCE DESCRIPTION: SEQ ID NO:8:

ACCACTGTTG TTTCCCAGGA AG 22

( 2 ) INFORMATION FOR SEQ ID NO:9:

( i ) SEQUENCE CHARACTERISTICS:
         ( A ) LENGTH: 25 base pairs
         ( B ) TYPE: nucleic acid
         ( C ) STRANDEDNESS: single
         ( D ) TOPOLOGY: linear ( i i ) MOLECULE TYPE: cDNA ( x i ) SEQUENCE DESCRIPTION: SEQ ID NO:9:

CCACCTTTTG ACAGTGATGA GAATG 25

( 2 ) INFORMATION FOR SEQ ID NO:10:

( i ) SEQUENCE CHARACTERISTICS:
         ( A ) LENGTH: 22 base pairs
         ( B ) TYPE: nucleic acid
         ( C ) STRANDEDNESS: single
         ( D ) TOPOLOGY: linear ( i i ) MOLECULE TYPE: cDNA ( x i ) SEQUENCE DESCRIPTION: SEQ ID NO:10:

```
CTAGGTTTGC CGAGTAGATC TC                                                     22
```

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
TTCCCTACTT CACAAGTCCG GAG                                                    23
```

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

```
GCCACTTCCT CCTCTTCGGC                                                        20
```

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

```
GTGGGAGTCA GACCCGTCAG                                                        20
```

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

```
CTATTGGTCT TCCTGGAAGT AGAAC                                                  25
```

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

```
CGCCCTTCTG GGAAAAGACC                                                        20
```

EXPRESSION OF HUMAN INTERLEUKIN-1β IN A TRANSGENIC ANIMAL

This is a continuation in part of U.S. Ser. No. 08/096,943 filed July 22, 1993, now abandoned.

FIELD OF THE INVENTION

The present invention relates to expression of human interleukin-1β by a transgenic animal.

BACKGROUND OF THE INVENTION

Human interleukin-1 (IL-1) consists of two proteins, IL-1α and IL-1β. Encoded by different genes (on the same chromosome), each is produced as a protein that is processed intracellularly by serine 31 kDa proteases and is secreted as a 15- to 17 kDa single-chain protein. The two secreted proteins have only limited amino acid sequence similarity (identity at only 25% to 40% of their positions, depending on the species). IL-1β, is the more abundant form, both at the level of mRNA and as a serum protein.

Produced in relatively large amounts by activated macrophages and monocytes, IL-1 is also synthesized by a variety of other cells, including keratinocytes, skin Langerhans cells, activated B cells, corneal epithelial cells, kidney mesangial cells, and large granular lymphocytes.

IL-1 exerts its effects on T and B cells primarily as a costimulator. It acts synergistically with IL-6 to stimulate the secretion of IL-2 and expression of IL-2 receptors on T cells when they respond to antigens and mitogens. IL-1 also enhances the stimulatory effects of IL-4 and IL-6 on the growth and differentiation of B cells.

The extensive effects of IL-1 on a wide variety of other cells and tissues account for many of the manifestations of acute and chronic infections and inflammation of immune origin. For instance, IL-1 causes fever by stimulating release of a pyrogen from the brain (hypothalamus), induces somnolence, diminishes appetite, augments the catabolic effects of the cytokine cachectin, and stimulates proliferation of granulocytes by inducing production of bone marrow colony-stimulating factors. In many of the diverse cells it affects, IL-1 enhances arachidonic acid breakdown into prostaglandins and, perhaps in some cells, into leukotrienes.

IL-1 is a major modulator of the immune response to trauma, infection, and inflammation. Endothelial cells exposed to IL-1 synthesize prostaglandins and platelet-activating factor and show accelerated release of von Willebrand factor. Interestingly, a significant increase in formation of prostaglandin $D_2$ in frontal cortex of Alzheimer's Disease patients has been described. Systemic administration of IL-1 results in increased hepatic production of serum amyloid A, a precursor of the amyloid fibrils found in a secondary amyloidosis.

IL-1 is expressed in the central nervous system where it is thought to play a number of roles, including a hypothalamic acute-phase response and a stimulation of astroglial proliferation after brain injury. Because of the diverse biological activities of IL-1, the observation that IL-1 enhances expression of the amyloid precursor protein (APP) mRNA transcripts in human endothelial cells is of particular importance. Goldgaber et al., (Interleukin 1 regulates synthesis of amyloid β-protein precursor mRNA in human endothelial cells, 1989, *Proc. Natl. Acad. Sci.* Vol 86: 7606–7610) described the increased level of IL-1 in brains of patients with Alzheimer's disease and Down's syndrome. Thus, the conditions that may lead to the increased expression of the APP gene are present in both diseases.

Experimental studies of the role of human interleukin-1β in disease would be facilitated by the existence of an appropriate animal model. Accordingly, it is an object of the present invention to provide an animal model in which human interleukin-1β expression can be regulated and measured. A animal model of the present invention is a transgenic mouse that expresses a functional human interleukin-1β gene in a regulated manner. The transgenic mice of the present invention are useful to identify compounds that affect chronic inflammation and Alzheimer's Disease. In addition, the transgenic mice of the present invention may be used to generate cell cultures.

SUMMARY OF THE INVENTION

A transgenic mouse expressing human interleukin-1β is provided. The transgenic mouse may be used to study chronic inflammatory diseases, Alzheimer's Disease and diseases in which IL-1β plays an essential role.

DETAILED DESCRIPTION OF THE INVENTION

The present invention relates to a transgenic animal that contains a gene encoding human interleukin-1β.

The term "animal" is used herein to include all vertebrate animals, except humans. It also includes an individual animal in all stages of development, including embryonic and fetal stages. A "transgenic animal" is any animal containing one or more cells bearing genetic information received, directly or indirectly, by deliberate genetic manipulation at a subcellular level, such as by microinjection or infection with a recombinant virus. The introduced DNA may be integrated within a chromosome, or it may be extra-chromosomally replicating DNA. The term "germ cell-line transgenic animal" refers to a transgenic animal in which the genetic information was introduced into a germ line cell, thereby conferring the ability to transfer the information to offspring. If such offspring in fact possess some or all of that information, then they, too, are transgenic animals.

The information may be foreign to the species of animal to which the recipient belongs, foreign only to the particular individual recipient, or genetic information already possessed by the recipient. In the last case, the introduced gene may be differently expressed than the native gene.

The genes may be obtained by isolating them from genomic sources, by preparation of cDNAs from isolated mRNA templates, by directed synthesis, or by some combination thereof.

To be expressed, the structural gene must be coupled to a promoter in a functional manner. Promoter or regulatory sequences may be used to increase, decrease, regulate or designate to certain tissues or to certain stages of development the expression of a gene. The promoter need not be a naturally-occurring promoter. The metallothionein-1 (MT-1) promoter is the promoter described in the preferred embodiment of the invention. The MT-1 promoter is sometimes described as being an inducible promoter. A more accurate description is semi-constitutive since the MT-1 promoter is always "on"; the activity of the MT-1 promoter is boosted by heavy metal ions.

The "transgenic non-human animals" of the invention are produced by introducing "transgenes" into the germline of the non-human animal. Standard techniques are employed; however, the art of generating a particular transgenic animal requires experimentation.

Embryonal target cells at various stages of development can be used to introduce transgenes. Different methods of introducing transgenes are used depending on the stage of development of the embryonal target cell. Generally, the zygote is the best target for micro-injection. In the mouse, the male pronucleus reaches the size of approximately 20 μm in diameter which allows reproducible injection of 1–2 pL of DNA solution. The use of zygotes as a target for gene transfer has a major advantage in that in most cases the injected DNA will be incorporated into the host gene before the first cleavage (Brinster, et al., (1985) *Proc. Natl. Acad. Sci. USA* 82 4438–4442). Consequently, nearly all cells of the transgenic non-human animal will carry the incorporated transgene. Generally, this will also result in the efficient transmission of the transgene to offspring of the founder since 50% of the germ cells will harbor the transgene. Microinjection of zygotes is the preferred method for incorporating transgenes in practicing the invention.

Retroviral infection can also be used to introduce a transgene into non-human animal. The developing non-human embryo can be cultured in vitro to the blastocyst stage. During this time, the blastomeres can be targets for retroviral infection (Jaenich, R. (1976) *Proc. Natl. Acad. Sci. USA* 73, 1260–1264). Efficient infection of the blastomeres is obtained by enzymatic treatment to remove the zona pellucida (Hogan et al., (1986) in Manipulating the Mouse Embryo, Cold Spring Harbor Laboratory Press, Cold Spring Harbor, N.Y.). Tie viral vector system used to introduce the transgene is typically a replication-defective retrovirus carrying the transgene (Jahner et al., (1985) *Proc. Natl. Acad. Sci. USA* 82, 6927–6931; Van der Putten et al., (1985) *Proc. Natl. Acad. Sci. USA* 82 6148–6152). Transfection is easily and efficiently obtained by culturing the blastomeres on a monolayer of virus-producing cells (Van der Putten, *supra;* Stewart et al., (1987) *EMBO J.* 6, 383–388).

Alternatively, retroviral infection can be performed at a later stage. Virus or virus-producing cells can be injected into the blastocoele (Jahner et al., (1982) *Nature* 298, 623–628). Most of the founder animals will be mosaic for the transgene since incorporation of the transgene occurs only in a subset of the cells which formed the transgenic non-human animal. Further, the founder animal may contain retroviral insertions of the transgene at a variety of positions in the genome; these generally segregate in the offspring. In addition, it is also possible to introduce transgenes into the germ line, albeit with low efficiency, by intrauterine retroviral infection of the midgestation embryo (Jahner et al., (1982) *supra*).

Another type of target cell for transgene introduction is the embryonal stem (ES) cell. ES cells are obtained from pre-implantation embryos cultured in vitro (Evans, M. J., et al., (1981) *Nature* 292, 154–156; Bradley, A., et al., (1984) *Nature* 309, 255–258; Gossler, et al., (1986) *Proc. Natl. Acad. Sci. USA* 83, 9065–9069; and Robertson, et al., (1986) *Nature* 322, 445–448). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal (For review see Jaenisch, R. (1988) *Science* 240, 1468–1474).

The methods for detecting the presence of the introduced DNA as well as measuring its expression are readily available and are well-known in the art. Such methods include, but are not limited to DNA hybridization, gel electrophoresis, Western Blots, histopathology, cell culture, microinjection, ES cell manipulation and polymerase chain reaction (PCR).

As used herein, a "transgene" is a DNA sequence introduced into the germline of a non-human animal by way of human intervention such as by way of the methods described above. The transgenes of the invention include DNA sequences which are capable of suppressing cognate endogenous alleles.

Attempts to express human interleukin-1β (IL-1β) in transgenic mice have had minimal success. There may be several reasons for this. First, IL-1β is toxic at relatively low concentrations. Second, IL-1β has been implicated in embryonic development and parturition. Third, IL-1β is produced as a precursor which is processed for release from specific types of cells (e.g., macrophages) by a specific mechanism.

To circumvent the physiological problems associated with overexpression of IL-1β, a regulated expression system was developed. The gene encoding human interleukin-1β was placed downstream of the murine metallothionein-1 (mMT-1) promoter. To assure mRNA stability an SV40-derived small T intron and poly A addition site were placed downstream of the IL-1β coding sequence. The mMT1 promoter is a semiconstitutive promoter; its expression levels are boosted by the addition of heavy metal ions such as a zinc and cadmium.

Human IL-1β expression may increase when the transgenic mice of the present invention are fed with zinc or cadmium.

A cell culture may be derived from the transgenic mice of the present invention by using techniques which are well-known in the art.

A potential therapeutic compound may be detected by measuring its capacity to affect IL-1β function in these transgenic mice. Such compounds may be formulated in accord with known methods to produce pharmaceutically acceptable compositions. Such compositions may be administered to patients in a variety of ways.

The following is presented by way of examples and is not to be construed as a limitation on the scope of the invention.

EXAMPLE 1

Construction of plasmid p12849-57-9
(metallothionein promoter-IL-1β gene)

Plasmid pMTK-BGH was derived from plasmid pMK (Brinster et al., *Cell*, Vol 27: 223–231). Plasmid pMTK was digested with KpnI and Bgl II and a 0.6 kb fragment containing the murine metallothionein-I (mMT) promoter was gel-isolated. The 0.6 kb promoter fragment was subcloned into the Kpn I-Bam HI site of pUC19 (New England Biolabs). The resulting plasmid was digested with XbaI, made flush-ended with T4 DNA polymerase and digested with HindIII. A blunt-HindIII, 3.3 kb pUC19-mMT vector fragment was gel-isolated.

Plasmid pHZ024 contains the SV40 small T intron and poly A sequences. Plasmid pHZ024 was prepared in the following manner.

Plasmid pBSHT1 contains a 8 kb EcoRI fragment of human Thy-1 gene (hThy-1) in pBSV (Van Rijs et al., *Proc. Natl. Acad. Sci. USA* 82, 5832–5835, (1985)).

The 3.7 kb EcoRI-BglIII fragment of pBSHT1 containing the hThy-1 promoter and the ATG translation initiation codon was cloned into the EcoRI-BamHI site of plasmid pTZ18u, and the resulting plasmid called was pHZ020.

The 1.6 kb BamHI-BglII fragment from pHZ020 containing the ATG initiation codon was cloned into the BamHI site of pTZ18u (pHZ021a). A PCR amplification was carried out using pHZ021a as a template and oligonucleotides T7 (in pTZ18u backbone) and oHZ002 (at the ATG initiation codon) as primers to generate a 1.3 kb product.

The sequence of the T7 primer is: 5'-TAA TAC GAC TCA CTA TAG GG-3' (SEQ ID NO:1).

The sequence of oHZ002 is:

```
5'-ACG TCG ACT CTA GAA GAT CTT CGA CTC GAG ATC
    GAT GGT ACC CGG GCA GGT TCA AGC TTC TGG GAT
    TGG GAT CTC AGT C-3'                    (SEQ ID NO:2)
```

The oHZ002 oligonucleotides destroyed the ATG codon and introduced a polylinker cloning site in the PCR product, as schematically outlined below:

```
5' - ACGTCGACTCTAGAAGATCTTCGACTCGAGATCGATGGT
     ACCCGGGCAGGTTCAAGCTTCTGGGATCTCAGTC - 3'
                                |  |
                5'-TCATGGTTCTGGGATCTCAGTC - 3' Wild-type
```

A NcoI partial digestion was performed on pHZ020 for cleavage at the downstream site. This was followed by a XbaI complete digestion which released the NcoI-XbaI fragment containing the ATG codon. The 1.3 kb PCR product was digested with NcoI-XbaI and inserted into the NcoI-XbaI-digested pHZ020 to form plasmid (pHZ022).

A BglII linker was inserted as the SmaI site upstream of SV40 small T intron of pSV2neo to form plasmid (pHZ023). (Southern, P. J. & Berg, P. J., *Mol. Appl. Genet.* 1,327, 1982.) A BglII linker, d(CAGATCTG), was used.

The 1.0 kb SV40 small T intron and polyA was isolated by BglII and BamHI digestion of plasmid pHZ023 and was ligated into the BglII-digested pHZ022. The resulting plasmid, pHZ024, contains two regulatory elements: the human Thy-1 promoter and the SV40 small T intron and polyA sequence.

Plasmid pHZ024 was digested with KpnI, made flush-ended with T4 DNA polymerase, and digested with HindIII. A blunt to HindIII, (approximately 0.9 kb) SV40 fragment containing the small T and poly A sequence was gel-isolated and ligated with the blunt-HindIII, 3.3 kb pUC19-mMT vector fragment described above to yield plasmid UC19-mMT-SV40 poly A.

Plasmid pUC19-mMT-SV40 poly A was digested with ClaI and BglII, which cut between the mMT promoter and SV40 poly A sequences.

Two synthetic oligodeoxynucleotides were annealed to form a 86-bp linker with the following structure:

```
5' - CGATGGAACCATGGAAATCTGCAGGGGACCTTACAGTCACCTAATCTCTCTCCTTCT
3' -     TACCTTGGTACCTTTAGACGTCCCCTGGAATGTCAGTGGATTAGAGAGAGGAAGA

CATCCTTCTGTTTCATTCAGAGGCAGCCTGC - 3'

GTAGGAAGACAAAGTAAGTCTCCGTCGGACG - 5'                (SEQ ID NO. 3)
```

This linker contains a ClaI sticky end, 5-base pair (bp) of untranslated leader sequence from the human Thy-1 gene (Seki, T., et al.,*PNAS* 82, 6657–6661, 1985), ATG codon (underlined), 17-bp of rat IL-1 receptor antagonist (IL-1ra) signal peptide sequence and the remaining 58-bp of the IL-1ra signal peptide sequence from mouse. The chimeric rat/mouse IL-1ra signal peptide sequence was used because the first 17-bp of the mouse sequence was unknown.

The gene encoding the mature form of the human IL-1β was constructed using polymerase chain reaction (PCR). The template DNA for PCR was plasmid pGEM-Blue/human IL-1β (gift of Andrew Howard, Merck Research Laboratories, Rahway, N.J.). This plasmid contains the cDNA encoding the mature form of human IL-1β. pGEM-Blue/human IL-1β was constructed by subcloning the EcoRI-AccI IL-1β DNA fragment from pKK223-3/hIL-1β (Tocci, M. J., et al., *Journal of Immunology* 138, 1109–1114, 1987) into the EcoRI-AccI digested pGEM-Blue vector (Promega, Inc.). It is apparent to those skilled in the art that pKK223-3/hIL-1β could also be used as template DNA for PCR.

The PCR-primers had the following sequences:

5' - GCACCTGTACGATCACTGAACTGC - 3'          (SEQ ID NO: 4)

(SEQ ID NO: 5)
5' - GAAGATCTAGGAAGACACAAATTGCATGGTGAAG - 3'

Following PCR, the 0.5 kb IL-1β gene fragment was made flush-ended with T4 DNA polymerase, digested with BglII (which cuts after the stop codon), gel-isolated and phosphorylated with T4 polynucleotide kinase.

The gel-isolated ClaI-BglII 4.2 kb vector fragment from pUC19-mMT-SV40-polyA was ligated with the 86-bp ClaI-blunt linker encoding the L-1ra signal peptide and the 0.5 kb blunt-BglII mature human IL-1βgene in a three-way ligation. The resulting plasmid, p12849-57-9 was sequenced using dideoxynucleotide sequencing.

To prepare the DNA cassette for microinjection, a large-scale CsCl plasmid prep of p12849-57-9 was prepared. The plasmid was digested with EcoRI and XbaI and electrophoresed through a 1% low melting point agarose gel containing 10 ng/ml ethidium bromide. The DNA was visualized using minimal exposure to short-wave UV light and the 2.1 kb DNA band was excised, melted at 65°–70° C., phenol/chloroform extracted 3X, chloroform extracted 1X and ethanol precipitated in 0.2 M NaCl. Following several 70% ethanol washes, the DNA was resuspended in 10 mM Tris, 0.25 mM ethylenediamine tetraacetic acid (EDTA), pH 7.5 and filtered through a pre-rinsed 0.2 μm cellulose acetate filter. The 2.1 kb, linear DNA fragment #12849-112-3 containing the mMT promoter, rat/mouse IL-1ra signal sequence, mature human IL-1β gene and SV40 small T intron and poly A was subsequently used for microinjection.

A sample of plasmid p12849-57-9 in a host *Escherichia coli* deposited under the Budapest Treaty in the American Type Culture Collection, 12301 Parklawn Drive, Rockville, Md. 20852, USA on Aug. 5, 1997 and has been assigned accession number ATCC 98500.

All restriction endonucleases and DNA modifying enzymes were from Boehringer Mannheim, Inc. DNA sequencing was performed using either Sequenase (U.S. Biochemical, Inc.) or ds DNA Cycle Sequencing Kit (BRL, Inc.). Oligodeoxynucleotides were synthesized on ABI DNA Synthesizer model #381A. PCR was according to Perkin-Elmer Corp.

EXAMPLE 2

Production of transgenic mice containing human IL-1β under regulation of MT-1 promoter Toxicity test experiments were performed to determine whether the p12849-57-9 DNA of Example 1 was toxic to the mouse embryos and to determine the optimal concentration to be used in microinjecting the DNA.

The $LD_{50}$ of p12849-57-9 was 5 ng/μL; therefore $5\times10^{-9}$ μg of p12849-57-9 DNA was microinjected into the pronucleus of one-cell fertilized mouse embryos obtained from superovulated B6SJL females. The embryos injected with the optimal concentration of the DNA were surgically reimplanted into the oviducts of pseudopregnant recipient mice and allowed to develop to term. At three to four weeks postnatal, tail samples were taken by clipping off approximately 1 cm. of tail for DNA dot blot assay to determine the presence of the transgene. Young pups were closely observed daily starting from PN1 (postnatal day 1) for pathological symptoms. Necropsies and/or biopsies were performed to collect tissue specimens for histological and for expression studies.

EXAMPLE 3

Analysis Of Transgenic Mice

DNA analysis

The pups derived from microinjected eggs of Example 2 were weaned at about 4 weeks of age. At that time a small segment (about 1 cm long) was removed from the distal end of the tail and used for DNA analysis. Genomic DNA was extracted from the tail samples and applied to a Gene Screen Plus® membrane filter using a dot blot apparatus. The filter was then hybridized with a $^{32}$P-labeled probe containing SV40 sequence which is present in the 3' area of the transgene. Since the endogenous mouse DNA does not contain the SV40 sequence, this probe is specific for the transgene and can be used to detect as little as 0.1 copies of the transgene in the mouse genome. Transgenic founders identified by DNA dot blot procedure were bred to produce progeny for further studies.

h IL-1β m RNA analysis

Human IL-1β mRNA can be detected by several different methods.

First, RNA-PCR may be used.

mMT-IL-1β transgenic animal tissues were analyzed for specific mRNA transcription using RNA-polymerase chain reaction (RNA-PCR). Following dissection, mouse tissues were immediately frozen on dry ice and stored at −70° C. Frozen samples were transferred in liquid nitrogen into a prechilled mortar, pulverized and transferred into tubes on dry ice. Total RNA was extracted as described (RNA Isolation Kit, product #200345; Stratagene, Inc.). Oligodeoxynucleotide primer pairs were synthesized for PCR with the following sequences:

1) 5'-GGCATTCCACCACTGCTCCCATT-3' SEQ ID NO:6 and
   5'-GCACCTGTACGATCACTGAACTGC-3' SEQ. ID NO:7
   for PCR detection of human IL-1β mRNA,
2) 5'-ACCACTGTTGTTTCCCAGGAAG-3' SEQ ID NO:8 and
   5'-CCACCTTTTGACAGTGATGAGAATG-3' SEQ ID NO:9
   for PCR detechon of mouse IL-1β mRNA,
3) 5'-CTAGGTTTGCCGAGTAGATCTC-3' SEQ ID NO:10 and
   5'-TTCCCTACTTCACAAGTCCGGAG-3' SEQ ID NO:11
   for PCR detection of mouse IL-6 mRNA,
4) 5'-GCCACTTCCTCCTCTTCGGC-3' SEQ ID NO:12 and
   5'-GTGGGAGTCAGACCCGTCAG-3' SEQ ID NO:13
   for PCR detection of mouse APP mRNA,
5) 5'-CTATTGGTCTTCCTGGAAGTAGAAC-3' SEQ ID NO: 14 and
   5'-CGCCCTCTGGGAAAAGACC-3' SEQ ID NO:15
   for PCR detection of mouse IL-1ra mRNA.

The oligonucleotides were designed to complement DNA sequences located within exons. Each oligonucleotide pair is separated by one or more introns in order to distinguish between genomic DNA and mRNA. The first primer of each pair corresponds to the "downstream" primer which is used for the reverse transcriptase portion of the RNA-PCR reactions. One μg of total RNA (determined by absorbance at 260 nm) was used for each RNA-PCR reaction as described (GeneAmp® RNA PCR Kit, product #N808-0017; Perkin Elmer Cetus, Corp.). The PCR was performed for 35 cycles with the following parameters per cycle: 95° C. for 1 min., 48° C. for 2 min., 72° C. for 2 min.

DNA bands of the appropriate sizes were visualized on a 1.2% agarose gel containing 0.5 μg/ml ethidium bromide. The relative mRNA levels (as determined by RNA-PCR) for the livers and kidneys of two mMT-IL-1β transgenic animals and a control non-transgenic animal are shown in Table 1.

TABLE 1

|  | LIVER | | | KIDNEY | | |
| --- | --- | --- | --- | --- | --- | --- |
|  | Trans. 1 | Trans. 2 | Control | Trans. 1 | Trans. 2 | Control |
| hIL-1β | +++ | ++ | − | ++ | − | − |
| mIL-1β | + | − | − | − | − | − |
| mIL-1ra | ++++ | ++++ | ++++ | ++++ | ++++ | ++ |
| mIL-6 | + | + | − | − | − | − |
| mAPP | ++ | ++ | ++ | +++ | +++ | +++ |

Second, RNase protection assays may be performed. Liver and other tissues were obtained from transgenic mice for isolation of mRNA. A $^{32}$P-labeled antisense RNA probe was used to hydridize hIL-1β mRNA in a solution hybridization reaction. The resulting double-stranded molecule is resistant to RNase digestion while unhybridized RNA will be digested by RNase treatment. The protected band was visualized by autoradiography after separation on a polyacrylamide gel. The results showed expression of the transgene in, liver and kidney tissues.

Third, in situ hybridizations were performed. Tissue sections were prepared from frozen brain and hybridized with a labeled oligonucleotide probe specific for hIL-1β mRNA followed by autoradiography. The results showed expression of the transgene in the cerebellum and the brain stem.

Fourth, histopathology studies were performed. Transgenic mice were necropsied to obtain brain and other tissues for pathology studies. Tissue samples are typically fixed in 10% formalin in phosphate buffered saline. Fixed tissues were sectioned and mounted on glass slides. The results showed inflammation of various tissues including the kidney, pancreas, lung, heart, vertebrae, leg joints and brain.

Finally, IL-1β protein analysis may be done. Blood plasma or homogenate of liver and other tissues is used for Enzyme Linked Immunoabsorbant Assay (ELISA) to measure hIL-1β concentrations in the tissues.

EXAMPLE 4

Cell Culture

The transgenic aminals of the present invention may be used as a source of cells for cell cultures. Tissues of transgenic mice are analyzed for the presence of human interleukin-1β. Cells of tissues carrying the human IL-1β gene may be cultured using standard methods that are well-known in the art and may be used to study human processing and expression of human IL-1β in cells.

EXAMPLE 5

Screening Assays

The animals of the present invention may be used to test compounds for the ability to reduce inflammation. A transgenic animal is treated with a test compound, in parallel with an untreated control animal. A comparatively reduced level of inflammation and neuropathology in the treated animal represents a positive result.

What is claimed is:

1. A transgenic mouse whose somatic and germ cells comprise and express a transgene comprising a murine metallothionein-1 promoter operably linked to a gene encoding human interleukin-1β, wherein said transgene is integrated into the genome of said cells, and wherein expression of said transgene results in chronic inflammation of the kidney and liver of said transgenic mouse.

2. The mouse of claim 1 wherein the transgene is p12849-57-9 (ATCC 98500).

3. A method for determining the ability of a compound to reduce inflammation comprising:

(a) treating the transgenic mouse of claim 1 with the compound; and (b) measuring inflammation in the treated transgenic mouse;

wherein a reduction of inflammation in said treated transgenic mouse indicates that said compound has the ability to reduce inflammation.

* * * * *